US011642076B2

(12) United States Patent
Dillon et al.

(10) Patent No.: US 11,642,076 B2
(45) Date of Patent: May 9, 2023

(54) ORAL APPLIANCE

(71) Applicant: UNIVERSITY COLLEGE DUBLIN, NATIONAL UNIVERSITY OF IRELAND, DUBLIN, Dublin (IE)

(72) Inventors: Frank Dillon, Dublin (IE); Eoin O'Cearbhaill, Dublin (IE); Kevin Krieger, Dublin (IE)

(73) Assignee: UNIVERSITY COLLEGE DUBLIN, NATIONAL UNIVERSITY OF IRELAND, DUBLIN, Dublin (IE)

(*) Notice: Subject to any disclaimer, the term of this patent is extended or adjusted under 35 U.S.C. 154(b) by 741 days.

(21) Appl. No.: 16/496,078

(22) PCT Filed: Mar. 21, 2018

(86) PCT No.: PCT/EP2018/057160
§ 371 (c)(1),
(2) Date: Sep. 20, 2019

(87) PCT Pub. No.: WO2018/172409
PCT Pub. Date: Sep. 27, 2018

(65) Prior Publication Data
US 2020/0008738 A1   Jan. 9, 2020

(30) Foreign Application Priority Data
Mar. 22, 2017   (GB) ..................... 1704545

(51) Int. Cl.
*A61B 5/00* (2006.01)
*A61F 5/56* (2006.01)
(52) U.S. Cl.
CPC .......... *A61B 5/4557* (2013.01); *A61B 5/4519* (2013.01); *A61B 5/486* (2013.01);
(Continued)

(58) Field of Classification Search
CPC .......... A61B 5/4557; A61B 2562/0247; A61B 5/682; A61B 5/228; A61F 5/56; A61F 5/556; A61F 2005/563
See application file for complete search history.

(56) References Cited

U.S. PATENT DOCUMENTS 4,715,367 A   12/1987   Crossley
4,842,519 A   6/1989   Dworkin
(Continued)

FOREIGN PATENT DOCUMENTS

WO   WO 2008104982 A2   9/2008
WO   WO 2010023655 A1   3/2010
(Continued)

OTHER PUBLICATIONS

PCT/EP2018/057160 International Search Report and Written Opinion dated Jun. 7, 2018, 10 pages.
(Continued)

*Primary Examiner* — David J. McCrosky
(74) *Attorney, Agent, or Firm* — Cozen O'Connor

(57) ABSTRACT

An oral appliance (100) comprising a sensing arrangement (101) disposed in proximity to at least one part of a facial muscle complex of a user. A method of controlling the oral appliance (100) comprising sensing, with the sensing arrangement (101), the at least one part of the facial muscle complex being brought towards the sensing arrangement; and in response to sensing the at least one part of the facial muscle complex being brought towards the sensing arrangement (101), controlling the oral appliance (100) to perform an action. An external processing unit (200) is arranged to interact with the oral appliance (100) in response to the oral appliance (100) performing the action.

13 Claims, 6 Drawing Sheets

(52) U.S. Cl.
CPC .......... *A61B 5/4836* (2013.01); *A61B 5/4839* (2013.01); *A61B 5/682* (2013.01); *A61B 2562/0247* (2013.01); *A61F 2005/563* (2013.01)

(56) References Cited

U.S. PATENT DOCUMENTS

| | | | |
|---|---|---|---|
| 5,078,153 A | 1/1992 | Norlander et al. | |
| 5,490,520 A | 2/1996 | Schafer et al. | |
| 6,089,864 A * | 7/2000 | Buckner | A61F 5/56 433/68 |
| 6,786,092 B2 * | 9/2004 | Nakao | A61B 5/228 73/379.03 |
| 11,317,857 B2 * | 5/2022 | Kahlert | A61B 5/682 |
| 2010/0036286 A1 | 2/2010 | Scholz et al. | |
| 2010/0204614 A1 | 8/2010 | Lindquist et al. | |
| 2011/0160618 A1 * | 6/2011 | Shemesh | A61F 5/56 600/590 |
| 2015/0038871 A1 | 2/2015 | Hatzilias et al. | |
| 2017/0035350 A1 | 2/2017 | Allessie | |

FOREIGN PATENT DOCUMENTS

| | | |
|---|---|---|
| WO | WO 2014074519 A1 | 5/2014 |
| WO | WO 2014110548 A1 | 7/2014 |
| WO | WO 2014110548 A4 | 7/2014 |

OTHER PUBLICATIONS

GB Patent Application No. 1618645.4 Search Report dated Sep. 18, 2017, 4 pages.

* cited by examiner

ORAL APPLIANCE

FIELD OF USE

The present invention is directed towards an oral appliance, method of controlling the oral appliance, and associated system.

BACKGROUND

One application of existing oral appliances is to assist in the determination of whether a user of the oral appliance suffers from bruxism—a condition characterised by forceful involuntary clenching or grinding of teeth. Bruxism can have significant detrimental consequences on the masticatory system. In severe cases, bruxism sufferers will experience symptoms such as dental sensitivity and pain. They can also suffer from headaches resulting from muscle tension, tenderness in the facial muscles and pain on opening the mouth due to damage of the temporomandibular joints. Reports of the incidence of bruxism within the dental community vary depending on the criteria employed, but it is generally agreed that around 10% of the population is affected by the condition.

Traditionally, the approach to the identification of bruxism has been clinical. A skilled dental professional will observe the dental area for signs of bruxism. These can include excessive wear on the biting surfaces of the teeth, cracked and broken teeth, cracked and broken restorations and sensitivity to palpation of the temporomandibular joints. This approach is generally ineffective as it is only able to identify the existence of bruxism after often significant damage to the dental area has emerged. As a result, bruxism is often only identified at a point where significant restorative dental treatment is required.

Approaches have been made to provide oral appliances which monitor biological parameters associated with bruxism. These oral appliances are promising as they can assist a user or dental professional to identify the existence of bruxism before significant dental wear/damage has occurred. However, these existing oral appliances are not entirely satisfactory.

One existing kind of oral appliance seeks to quantify the intensity and/or duration of bruxing by measuring the interocclusal pressure (i.e. the pressure between the occlusal surfaces of opposing teeth). These oral appliances require the placement of a measuring device between the upper and lower teeth of the user. This is done by providing a splint or mouth guard with the measuring device attached thereto. By definition, this kind of oral appliance alters the position of the user's jaws relative to each other whilst the patient is asleep. This may result in an involuntary change of the muscular activity of the user's masticatory system leading to inaccurate or false measurement results.

Another disadvantage of these interocclusal devices is that they are sometimes considered to be socially unacceptable due to their unsightly appearance, and can result in a speech impediment effect on the user. This means that these interocclusal devices can only really be used to measure the characteristics associated with bruxism during the night while the patient sleeps. Even then, the interocclusal device may disrupt the sleep of the user which may lead to reduced use of the interocclusal device.

Another existing kind of oral appliance involves placing EMG surface electrodes on the outside surface of the cheek of the user to sense the contraction of masticatory muscles such as the masseter and the temporalis. These EMG devices also have disadvantages. They are unsuitable for measuring the characteristics associated with bruxism during the day as they are impractical for at least social reasons. In addition, they are also uncomfortable for measuring the characteristics associated with bruxism during the night time as the person has to sleep with the EMG device attached to their face. Another disadvantage is that the EMG measurements may be affected by electronic noise produced by the sleeping user, such as due to muscle contractions caused by the user scratching or performing other movements during sleep. As a result, these EMG devices typically require detailed calibration of the gathered data in order to produce a meaningful result.

SUMMARY OF EMBODIMENTS

It is an objective of the present invention to overcome at least some of the problems associated with these existing oral appliances, or at least provide an alternative oral appliance.

Accordingly, the present invention provides a method of controlling an oral appliance, the oral appliance comprising a sensing arrangement disposed in proximity to at least one part of a facial muscle complex of a user, the method comprising: sensing, with the sensing arrangement, the at least one part of the facial muscle complex being brought towards the sensing arrangement; and in response to sensing the at least one part of the facial muscle complex being brought towards the sensing arrangement, controlling the oral appliance to perform an action.

Here, "facial muscle complex" refers to a muscle complex used to assist in at least one of chewing, clenching the jaw, and grinding the teeth. The "at least one part of a facial muscle complex" may comprise one or more of the masseter muscle complex, the temporalis muscle complex, the internal pterygoid muscle complex, and the buccinator muscle complex or at least one part thereof.

Here, "muscle complex" refers to the muscle and/or the tendons and other tissue matter associated with the muscle or at least one part thereof. For example, "muscle complex" may exclude teeth, that is "muscle complex" may not include teeth within its definition. For example, the "masseter muscle complex" refers to the masseter muscle and/or the tendons and other tissue matter associated with the masseter muscle or at least one part thereof.

Unlike the existing oral appliances, the oral appliance of the present invention does not measure the interocclusal pressure (i.e. the pressure between the occlusal surfaces of opposing teeth) or EMG signals, or directly measure the movement of teeth toward/away from one another. Instead, the oral appliance of the present invention is disposed in proximity to the at least one part of the facial muscle complex of the user and senses the at least one part of the facial muscle complex being brought towards the sensing arrangement. Advantageously, the oral appliance of the present invention is able to avoid problems associated with existing oral appliances.

The at least one part of the facial muscle complex being brought towards the sensing arrangement may be brought towards the sensing arrangement as a result of a deformation of the at least one part of the facial muscle complex. This may include a deformation of the masseter muscle complex or a part thereof.

Here, a "deformation" of the at least one part of the facial muscle complex may refer to a contraction or a relaxation of the at least one part of the facial muscle complex. In most examples, the deformation will be a contraction of the at least one part of the facial muscle complex, such as a contraction of at least one part of the masseter muscle complex.

Sensing the at least one part of the facial muscle complex being brought towards the sensing arrangement may comprise sensing an object interacting with the sensing arrangement as a result of the at least one part of the facial muscle complex being brought towards the sensing arrangement.

Sensing the at least one part of the facial muscle complex being brought towards the sensing arrangement may comprise sensing an object physically interacting with the sensing arrangement as a result of the at least one part of the facial muscle complex being brought towards the sensing arrangement.

Sensing the object physically interacting with the sensing arrangement may comprise sensing the object contacting the sensing arrangement.

The object may be a tissue of the user. The tissue may be an epithelial tissue of the user and may form at least part of the oral cavity of the user. The epithelial tissue may be at least part of the buccal tissue of the user.

Sensing the at least one part of the facial muscle complex being brought towards the sensing arrangement may comprise sensing one or more of whether the at least one part of the facial muscle complex has deformed, the number of deformations of the at least one part of the facial muscle complex over a period of time, the duration of one or more deformations of the at least one part of the facial muscle complex, and the degree of one or more deformations of the at least one part of the facial muscle complex.

Sensing the degree of one or more deformations of the at least one part of the facial muscle complex may comprise sensing the pressure exerted on the sensing arrangement as a result of the at least one part of the facial muscle complex being brought towards the sensing arrangement.

The sensing arrangement may comprise a switch which may be a mechanically activated switch. The switch may be activated in response to the at least one part of the facial muscle complex being brought towards the switch which may include the at least one part of the facial muscle complex physically interacting with the switch. The sensing arrangement may comprise a pressure sensor for detecting the extent with which the at least one part of the facial muscle complex is deformed. The sensing arrangement may comprise a capacitive sensor or a piezoelectric sensor.

The oral appliance may be mounted intra-orally. Advantageously, by having the oral appliance mounted intra-orally, the oral appliance is disposed within the user's mouth. The oral appliance is therefore not attached to the outer surface of the user's face and as a result does not have the disruptive, socially unacceptable problems present in existing EMG oral appliances.

The oral appliance may be mounted in a position that allows full centric occlusion. In other words, the oral appliance is mounted in a position that allows a user to close their jaw normally. Therefore, the oral appliance does not have the disruptive properties associated with existing interocclusal devices. The oral appliance may be mounted on the buccal aspect of the upper posterior teeth or in proximity thereto. That is, the oral appliance is arranged not to be located occlusally between teeth. The teeth can be clenched without contacting the oral appliance occlusally between teeth.

The oral appliance may be at least temporarily orally fixated in the user's mouth using an adhesive material. The adhesive material may be a resin, dental resin or other medical grade polymer. The oral appliance may be temporarily orally fixated to the user's mouth for more than one day, several weeks, or a period of approximately 30 days. In this way, the oral appliance can sense the at least one part of the facial muscle complex being brought towards the sensing arrangement for a relatively long period of time without any action by the user. The operation of the oral appliance is not reliant on the user remembering or being told to wear it as per the existing interocclusal and EMG devices.

Controlling the oral appliance to perform an action may comprise controlling the oral appliance to generate a signal for transmission or storage. Controlling the oral appliance to generate a signal may comprise processing the sensing data received from the sensing arrangement. Processing the sensing data may comprise converting the sensing data from an analogue to a digital format.

The signal may indicate one or more of whether the at least one part of the facial muscle complex has deformed, the number of deformations of the at least one part of the facial muscle complex over a period of time, the duration of one or more deformations of the at least one part of the facial muscle complex, and the degree of one or more deformations of the at least one part of the facial muscle complex.

Controlling the oral appliance to perform an action may comprise controlling the oral appliance to transmit the signal to an external processing unit.

The signal may indicate whether the user has bruxism-like conditions. A dental professional or user of the oral appliance may be able to interpret the transmitted signal data to determine whether the user is suffering from bruxism.

The external processing unit may be adapted to process the received signal data to indicate whether at least one of a jaw clenching, teeth grinding or chewing event has occurred. The external processing unit may be adapted to process the received data to indicate whether the user has bruxism-like conditions. The external processing unit may compare the received signal data against one or more predetermined sets of bruxism determination criteria.

Controlling the oral appliance to transmit the signal may comprise controlling the oral appliance to transmit the signal to the external processing unit over a wireless network.

Controlling the oral appliance to perform an action may comprise controlling the oral appliance to store the signal in a storage unit of the oral appliance. The method may further comprise processing the sensing data received from the sensing arrangement to indicate whether at least one of a jaw clenching, teeth grinding, or chewing event has occurred. The method may further comprise processing the sensing data by comparing the sensing data against one or more predetermined sets of bruxism determination criteria.

Controlling the oral appliance to perform an action may comprise controlling an actuator of the oral appliance.

Controlling the oral appliance to perform an action may comprise controlling the oral appliance to trigger the generation of a stimulus in response to sensing the at least one facial muscle complex being brought towards the sensing arrangement. Controlling the oral appliance to trigger the generation of a stimulus may comprise controlling the oral appliance to trigger the activation of the actuator to apply a stimulus to the user. Controlling the oral appliance to trigger the generation of a stimulus may comprise controlling the oral appliance to trigger the activation of an actuator of a separate external processing unit. The actuator may generate a vibrational stimulus, an electrical stimulus, or an alarm which may be an audible alarm.

The actuator may comprise an applicator. The applicator may comprise one or more needles or microneedles. Controlling the applicator of the oral appliance may comprise controlling the applicator to apply medicament to the user in response to the sensing arrangement sensing the at least one part of the facial muscle complex being brought towards the sensing arrangement.

The at least one part of the facial muscle complex may comprise at least one part of the masseter muscle complex.

Accordingly, the present invention further provides an oral appliance adapted to be controlled by any of the methods as outlined above.

Accordingly, the present invention further provides an oral appliance comprising: a sensing arrangement adapted to be disposed in proximity to at least one part of a facial muscle complex of a user; and a controller adapted to control the oral appliance to perform an action in response to the sensing arrangement sensing the at least one part of the facial muscle complex being brought towards the sensing arrangement.

The oral appliance may be adapted to be at least temporarily orally fixated in the mouth of the user.

The oral appliance may comprise an adhesive material for at least temporarily orally fixating the oral appliance in the mouth of the user. The adhesive may be a resin, dental resin, or medical grade polymer.

The sensing arrangement may comprise a switch which may be a mechanically activated switch. The switch may be adapted to be activated in response to the at least one part of the facial muscle complex being brought towards the switch. The sensing arrangement may comprise a pressure sensor adapted to detect the extent with which the at least one part of the facial muscle complex is deformed. The sensing arrangement may comprise a capacitive sensor or a piezoelectric sensor.

The oral appliance may comprise a power source for powering the oral appliance. The power source may be a battery. The battery may be rechargeable. The battery may be rechargeable using wireless power transfer.

The controller may be adapted to control the oral appliance to generate a signal for transmission or storage. The controller may be adapted to control the oral appliance to generate a signal by processing the sensing data received from the sensing arrangement. The processing of the sensing data may comprise converting the sensing data from an analogue to a digital format.

The signal may indicate one or more of whether the at least one part of the facial muscle complex has deformed, the number of deformations of the at least one part of the facial muscle complex over a period of time, the duration of one or more deformations of the at least one part of the facial muscle complex, and the degree of one or more deformations of the at least one part of the facial muscle complex.

The oral appliance may comprise a processor for processing sensing data received from the sensing arrangement. The processor may comprise an analogue-to-digital convertor. The processor may be adapted to process the sensing data to determine whether at least one of a jaw clenching, teeth grinding or chewing event has occurred.

The oral appliance may comprise a storage unit for storing the generated signal.

The oral appliance may further comprise a transmitter. The controller may be adapted to control the transmitter to transmit a signal to an external processing unit in response to the sensing arrangement sensing the at least one part of a facial muscle complex being brought towards the sensing arrangement.

The oral appliance may be used to indicate whether the user has bruxism-like conditions. Advantageously, the oral appliance transmits sensing data to the external processing unit in response to the at least one part of the facial muscle complex being brought towards the sensing arrangement. The sensing data indicates one or more of whether at least one part of the facial muscle complex has deformed, the number of deformations of the at least one part of the facial muscle complex over a period of time, the duration of one or more deformations of the at least one part of the facial muscle complex, and the degree of one or more deformations of the at least one part of the facial muscle complex. The external processing unit can process this data to determine whether the user has bruxism-like symptoms. Alternatively or additionally, the processing capabilities may be provided in the oral appliance such that the oral appliance can process the sensing data to determine whether the user has bruxism-like conditions. Determining whether the user has bruxism-like conditions may comprise comparing the sensing data to a predetermined set of standard bruxism criteria.

The oral appliance may be adapted to generate a stimulus in response to sensing the at least one facial muscle complex being brought towards the sensing arrangement. The oral appliance may activate an actuator to apply a physical stimulus to the user in response to the at least one part of the facial muscle complex being brought towards the sensing arrangement. The actuator may be part of the oral appliance or may be part of a separate external processing unit. The actuator may generate a vibrational stimulus, an electrical stimulus, or an alarm which may be an audible alarm.

The oral appliance may be used to control an external processing unit to perform an action. The oral appliance may be adapted to transmit a signal for controlling the external processing unit in response to the sensing arrangement detecting the at least one part of the facial muscle complex being brought towards the sensing arrangement. Advantageously, the oral appliance may be used as an assistive technology device. This may have application for users suffering from neuromotor disorders. Such users may be able to use the oral appliance as a clench activated clicker for controlling the external processing unit. The external processing unit may be a computing device running dedicated assistive software programmes or may be a dedicated assistive device. Users with neuromotor disorders often having limited muscular function, and therefore the oral appliance may enable more efficient use of the voluntary muscular activity available to them.

The oral appliance may further comprise an actuator. The controller may be adapted to control the actuator in response to the sensing arrangement sensing the at least one part of the facial muscle complex being brought towards the sensing arrangement.

The actuator may be an applicator. The controller may be adapted to control the applicator to apply medicament to the user in response to the sensing arrangement sensing the at least one part of the facial muscle complex being brought towards the sensing arrangement. The applicator may comprise one or more needles. The applicator may comprise microneedles.

Advantageously, the oral appliance may be used as drug delivery device. The drug delivery may be initiated voluntarily by the user in response to the user bringing their at least one part of the facial muscle complex towards the sensing arrangement such as by clenching their jaw. In addition, the drug delivery may be initiated when the user involuntarily moves their at least one part of the facial muscle complex towards the sensing arrangement. This involuntary movement may be due to the user suffering from a seizure which results in the user's jaw clenching.

The oral appliance may be positioned intra-orally in a position such that the oral appliance contacts buccal tissue when the at least one part of the facial muscle complex is brought towards the sensing arrangement. The oral appliance may be positioned on the buccal aspect of the posterior teeth. Advantageously, this enables the oral appliance to act as a transbuccal drug delivery device. The oral appliance may comprise microneedles to advantageously facilitate optimal transbuccal drug delivery.

The oral appliance may be used to indicate whether the user is suffering from epilepsy-like conditions. User's suffering from epilepsy may experience nocturnal seizures which involve clenching of the jaw during sleep. Advantageously, the oral appliance is able to detect this clenching of the jaw by detecting the at least one part of the facial muscle complex being brought towards the sensing arrangement. The oral appliance is therefore able to help indicate whether the user is suffering from epilepsy like conditions.

The oral appliance may be used to assist in the treatment of epilepsy. The oral appliance may be adapted to perform an action involving applying a medicament to the user in response to the oral appliance or an external processing unit which receives the sensing data from the oral appliance determining that the user is suffering from epilepsy-like conditions. The medicament may be applied by an applicator of the oral appliance or by the external processing unit. The external processing unit may be adapted to apply the medicament in response to receiving a command from the oral appliance.

The oral appliance may have dimensions in the region of 20 mm×10 mm×5 mm.

Accordingly, the present invention further provides a system comprising any of the oral appliances as outlined above; and an external processing unit arranged to interact with the oral appliance in response to the oral appliance performing the action.

The external processing unit may be a mobile device or a dedicated device.

The external processing unit may be adapted to perform an action in response to receiving the sensing data from the oral appliance.

The external processing unit may be adapted to process the received sensing data to determine whether a bruxism event has occurred. Processing the received data may comprise comparing the data against a predetermined set of bruxism criteria.

BRIEF DESCRIPTION OF THE FIGURES

For a better understanding of the invention, and to show how embodiments of the same may be carried into effect, reference will now be made, by way of example only, to the accompanying diagrammatic drawings in which.

DETAILED DESCRIPTION OF THE EMBODIMENTS

Figure 1:
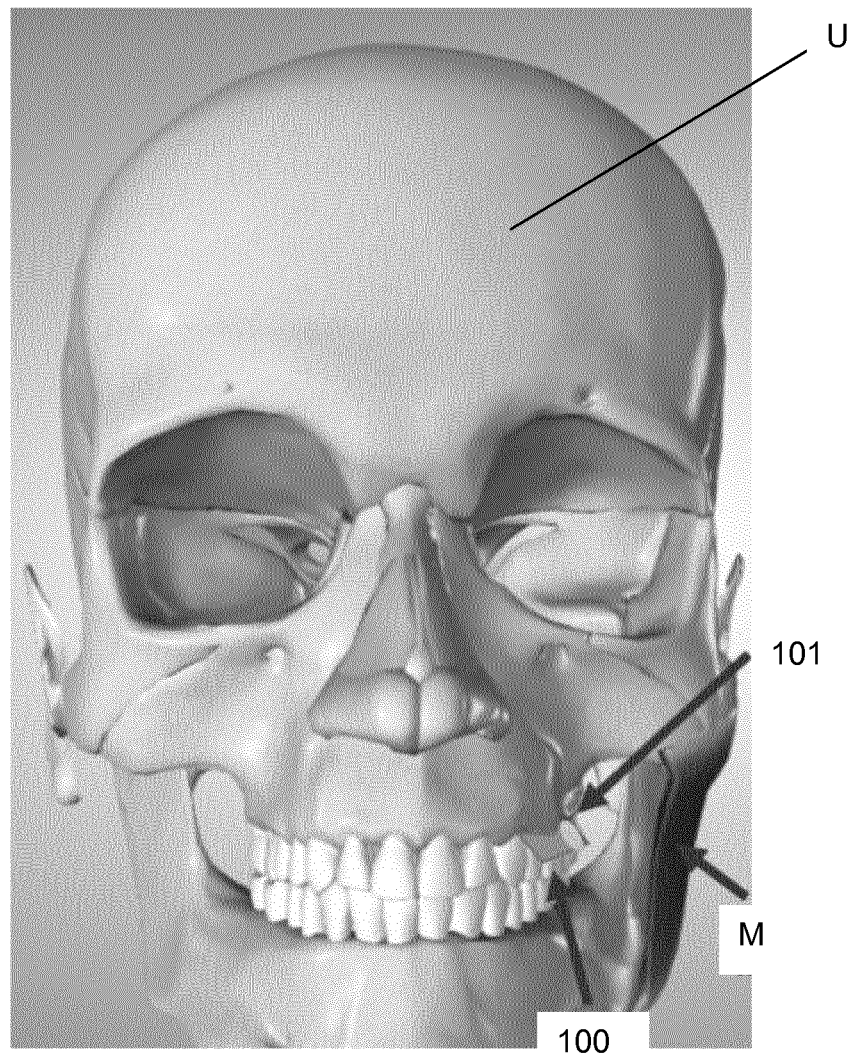
FIG. 1 is a front elevation of an oral appliance mounted intra-orally in accordance with an example embodiment.

Referring to FIG. 1, there is shown an oral appliance indicated generally by the reference numeral 100. The oral appliance 100 is shown mounted intra-orally in a user U. The user U is generally intended to be a living person, and it will be appreciated that the skeletal view of the user U is just so that the oral appliance 100 is visible in the drawings. The oral appliance 100 of the present invention is not limited to use in humans, and could be used in other mammals or animals with a masticatory system, as appropriate.

The oral appliance 100 comprises a sensing arrangement 101. The sensing arrangement 101 is mounted in proximity to at least one part of a facial muscle complex of the user U. In FIG. 1, the oral appliance 100 is mounted in the left-hand side of the mouth of the user U and the sensing arrangement 101 is in proximity to the masseter muscle complex M. The masseter muscle complex M is part of the facial muscle complex. The present invention is not limited to this arrangement. The oral appliance 100 may be mounted in proximity to another part of a facial muscle complex, such as the internal pterygoid muscle complex or the buccinator muscle complex or at least one part thereof.

The sensing arrangement 101 is adapted to sense the at least one part of the facial muscle complex being brought towards the sensing arrangement 101. In response to sensing the at least one part of the facial muscle complex being brought towards the sensing arrangement 101, the oral appliance 100 is adapted to be controlled to perform an action. The at least one part of the facial muscle complex is brought towards the sensing arrangement 101 when the at least one part of the facial muscle complex contracts. In particular, as the at least one part of the facial muscle complex contracts, the muscle complex deforms and changes in dimension such that it moves towards the sensing arrangement 101. The at least one part of the facial muscle complex contracts when the user U is chewing, clenching their jaw, or grinding their teeth. As a result, the oral appliance 100 is able to sense these chewing, clenching, and grinding events and perform an action as a result of sensing when the at least one part of the facial muscle complex is brought towards the sensing arrangement.

One known type of existing oral appliance detects chewing, clenching, and grinding events by measuring the interocclusal pressure (i.e. the pressure between the occlusal surfaces of opposing teeth). This is a logical way to directly detect chewing, clenching and grinding events. That is because it is logical that the user chewing, clenching or grinding their teeth will result in an increase in the interocclusal pressure. Another known type of existing oral appliance detects chewing, clenching, and grinding events by measuring the EMG signals of the user. This is a logical way to indirectly detect chewing, clenching and grinding events. That is because it is logical that the facial muscles will have increased electrical activity during chewing, clenching and grinding events.

The oral appliance 100 of the present invention, however, provides a counter-intuitive and surprising way to sense chewing, clenching and grinding events. In particular, the inventors of the present invention cleverly realised that the facial muscles may undergo quite significant changes in dimensions during muscular contraction. Further, the inventors of the present invention cleverly realised that these changes in dimensions can be utilized by providing a sensing arrangement 101 disposed in proximity to the at least one part of the facial muscle complex to sense the at least one part of the facial muscle complex being brought towards the sensing arrangement 101. This is an entirely different approach to current approaches for sensing chewing, clenching and grinding events. This different approach means that the oral appliance 100 does not need to measure the interocclusal pressure or EMG signals. Advantageously, the oral appliance 100 is able to avoid problems associated with these existing oral appliances.

Referring to FIG. 1, the oral appliance 100 is shown positioned intra-orally, that is within the mouth of the user U. Mounting the oral appliance 100 intra-orally is advantageous as it avoids the user U having to 'wear' the oral appliance 100 on their face which can be embarrassing and uncomfortable for the user U. The oral appliance 100 is able to be used all day, i.e. during both the daytime and at night when the user U is sleeping. This advantageously means that the clenching, chewing, and grinding events can be detected during both the day and the night. The oral appliance 100, however, does not have to be mounted intra-orally, and in some embodiments may be positioned externally such as on the external cheek of the user U if desired. It is believe that intra-oral use may be beneficial for measurement accuracy and/or comfort and/or aesthetic reasons.

The sensing arrangement 101 is adapted to sense the at least one part of the facial muscle complex being brought towards the oral appliance 100 by sensing an object physically interacting or contacting the sensing arrangement 101 as a result of the at least one part of the facial muscle complex being brought towards the oral appliance 100. In one particular example shown in FIG. 1, the sensing arrangement 101 is positioned such that as the masseter muscle complex M contracts, the buccal tissue of the user U is brought towards and contacts the sensing arrangement 101. The sensing arrangement 101 is therefore able to sense one or more of whether the at least one part of the facial muscle complex has deformed, the number of deformations of the at least one part of the facial muscle complex over a period of time, the duration of one or more deformations of the at least one part of the facial muscle complex, and the degree of one or more deformations of the at least one part of the facial muscle complex.

The sensing arrangement 101 in one example is a switch 101. The switch 101 is able to sense whether the at least one part of the facial muscle complex has deformed and/or the number of deformations of the at least one part of the facial muscle complex over a period of time. In particular, as the at least one part of the facial muscle complex contracts, the at least one part of the facial muscle complex deforms and moves towards the switch 101. As the at least one part of the facial muscle complex approaches the switch 101, the switch 101 is activated to thereby detect the deformation of the at least one part of the facial muscle complex. Over time, the switch 101 can detect the number of deformations of the at least one part of the facial muscle complex. The switch 101 in some examples is also able to sense the duration of the deformations of the at least one part of the facial muscle complex. In particular, the oral appliance 100 is able to determine the duration of time in which the switch 101 is continuously in the ON-state. In this way, the oral appliance 100 is able to determine the number and frequency of the clenching, chewing, and grinding events.

The sensing arrangement 101 in another example is a pressure sensor 101. The pressure sensor 101 is able to sense the degree/the extent of one or more deformations of the at least one part of the facial muscle complex. In particular, as the at least one part of the facial muscle complex contracts, the at least one part of the facial muscle complex deforms and moves towards the pressure sensor 101. As the at least one part of the facial muscle complex approaches the pressure sensor 101, the pressure sensor 101 is able to sense the force exerted on the pressure sensor 101 as a result of the at least one part of the facial muscle complex detecting. In this way, the oral appliance 100 is able to determine the forcefulness of the clenching, chewing, and grinding events. The pressure sensor 101 in some examples is also able to sense the number of deformations and/or the duration of the deformations.

It will be appreciated that in some examples, the sensing arrangement 101 may comprise both the switch 101 and the pressure sensor 101. Additionally or separately, the sensing arrangement 101 may comprise a capacitive sensor 101 or a piezoelectric senor 101.

Figure 2:
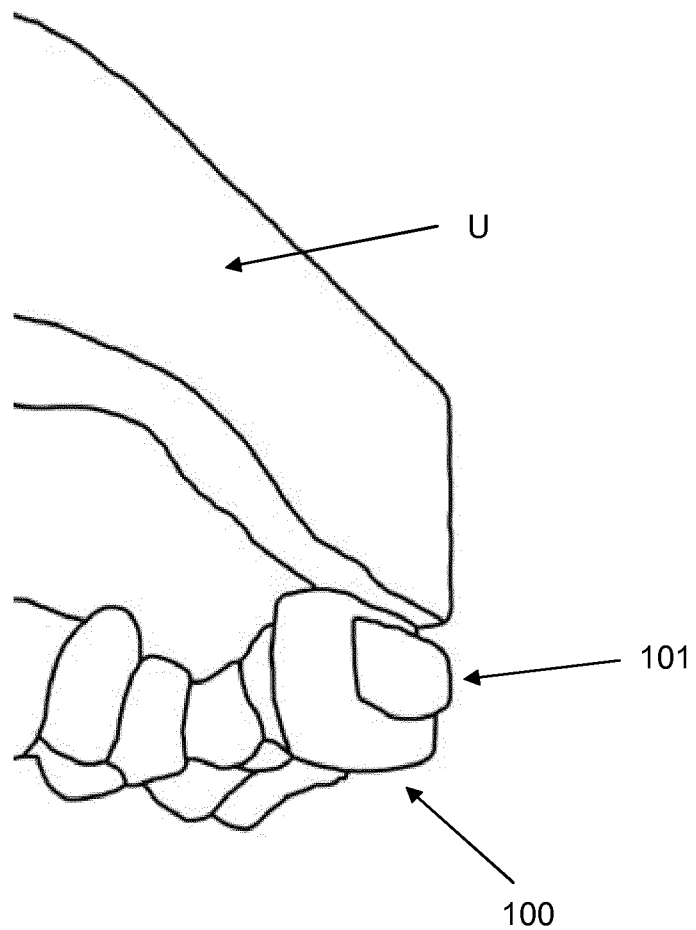
FIG. 2 is a perspective view of an oral appliance mounted intra-orally in accordance with an example embodiment.

Referring to FIG. 2, the oral appliance 100 is mounted intra-orally in a position that allows full centric occlusion. In particular the oral appliance 100 is mounted to the buccal aspect of the upper posterior teeth. This position helps enable the oral appliance 100 sense at least part of the masseter muscle complex M being brought towards the sensing arrangement 101. Mounting the oral appliance 100 in a position that allows full centric occlusion is significant as it allows the user U to close their jaw normally. Therefore, the oral appliance 100 does not have the disruptive properties associated with existing interocclusal and EMG devices. In addition, the masseter muscle complex has been found by the inventors of the present invention to undergo significant changes in dimensions during contraction, and therefore can provide clear and easily measureable indications of whether the user U is clenching, grinding or chewing.

Figure 3:
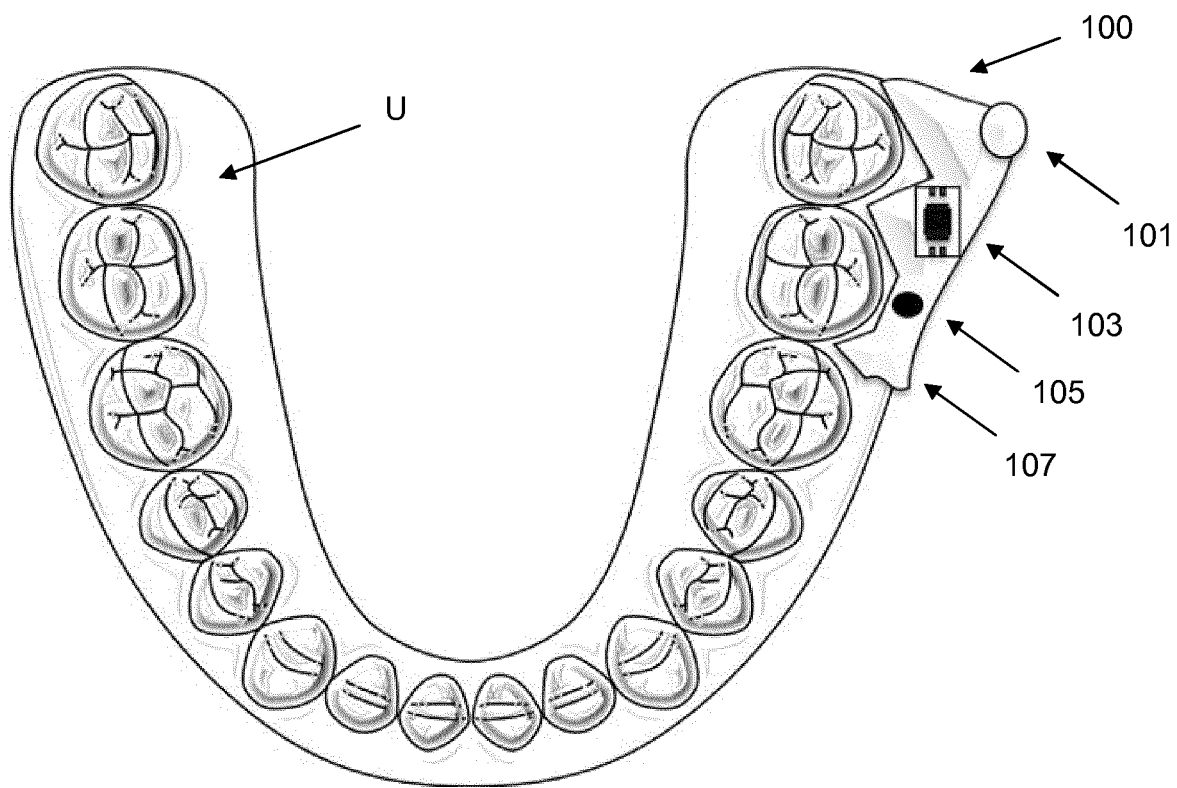
FIG. 3 is a bottom elevation of an oral appliance mounted intra-orally in accordance with an example embodiment.

Referring to FIG. 3, there is provided a detailed view of the oral appliance 100 mounted to the buccal aspect of the upper posterior teeth. The oral appliance 100 comprises the sensing arrangement 101, circuit 103, a power source 105, and an adhesive material 107. The adhesive material 107 acts to fixate the oral appliance 100 in the desired position in the mouth of the user U. The sensing arrangement 101 and/or circuit 103 and/or power source 105 are embedded in the adhesive material 107. The adhesive material 107 is a resin, dental resin or other medical grade polymer. The adhesive material 107 is used to at least temporarily orally fixate the oral appliance 100 in the mouth of the user U. In some arrangements, the oral appliance 100 is temporarily orally fixated in the mouth of the user U for several days, weeks, or for a period of approximately 30 days. By continuously mounting the oral appliance 100 in the mouth of the user U for a period of time, the oral appliance 100 is able to sense the chewing, clenching, and grinding events over a long period of time. Unlike interocclusal and EMG devices, the oral appliance 100 is not reliant on the user U remembering or being told to wear it. Therefore, more accurate and consistent measurement results can be obtained by the oral appliance 100.

Figure 4:
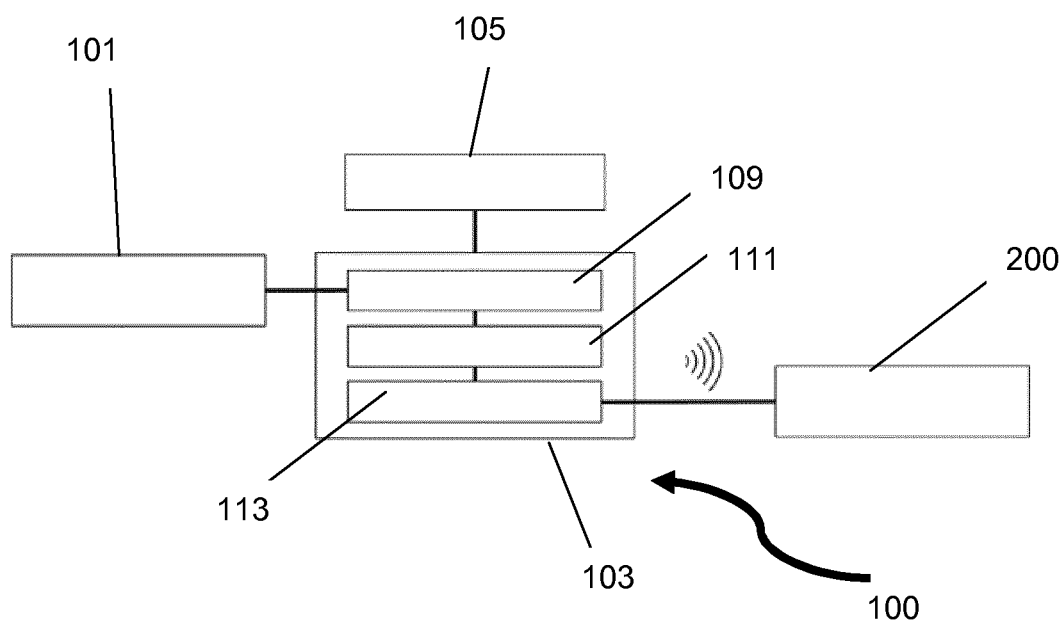
FIG. 4 is a simplified schematic diagram of a system comprising an oral appliance in accordance with an example embodiment.

Referring to FIG. 4, there is shown a schematic view of the components of the oral appliance 100 according to an example embodiment. The oral appliance 100 comprises the sensing arrangement 101, circuit 103, and power source 105.

In this example arrangement, the circuit 103 is a microchip 103 that comprises a processor 109, a controller 111, and a transmitter 113. It will be appreciated that this is only one example structure. The circuit 103 is entirely optional, and instead, one or more of the processor 109, controller 111, and transmitter 113 may be provided as separate units. In addition, the processor 109 and transmitter 113 may be integrated into the controller 111. That is, the controller 111 may perform all of the functionality of the processor 109 and the transmitter 113.

The controller 111 of FIG. 4 is shown as a microcontroller 111. This is only one example arrangement. The controller 111 may also be provided a hardware device, such as circuitry in the form of discrete or integrated components, a Field Programmable Gate Array (FPGA) or Application Specific Integrated Circuit (ASIC), which performs certain tasks or provides the associated functionality.

In one example, the controller 111 controls the oral appliance 100 to generate a signal for transmission or storage. The signal indicates one or more of whether the at least one part of the facial muscle complex has deformed, the number of deformations of the at least one part of the facial muscle complex over a period of time, the duration of one or more deformations of the at least one part of the facial muscle complex, and the degree of one or more deformations of the at least one part of the facial muscle complex.

In one example, the processor 109 processes the sensing data received from the sensing arrangement 101. In the example as shown in FIG. 4, the processor 109 is an analogue-to-digital convertor 109, and processing the sensing data comprises converting the sensing data from an analogue format to a digital format.

In the example shown in FIG. 4, the controller 111 is adapted to control the transmitter 113 to transmit the signal. The transmitter 113 is shown as an RF transmitter 113. It will be appreciated that this is just one example, and that other forms of transmitter 113 are within the scope of the present invention. The transmitter 113 in most examples will transmit the signal over a wireless communication protocol. The wireless communication protocol will in most examples be a local wireless communication protocol. In some examples, the local wireless communication protocol will be a BLUETOOTH® protocol such as BLUETOOTH® Low Energy. Other forms of local wireless communication protocol are within the scope of the present invention. The transmitter 113 transmits the signal to an external processing unit 200. In FIG. 4, the external processing unit 200 is shown as a dedicated receiver/mobile phone 200. It will be appreciated that this is just one example, and that other forms of external processing unit 200 are within the scope of the present invention. The oral appliance 100 and external processing unit 200 form a system.

Figure 5:
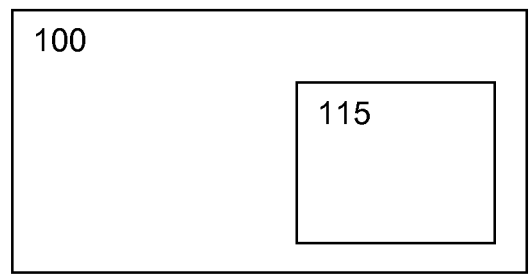
FIG. 5 is a simplified schematic diagram of an oral appliance in accordance with an example embodiment.

Referring to FIG. 5, in one example the oral appliance 100 comprises a storage unit 115 for storing the signal. The stored signal may be subsequently transmitted to the external processing unit 200 using the transmitter 113. In some examples, the processor 109 (FIG. 4) is able to process the signal to determine whether at least one of a clenching, grinding or chewing event has occurred.

In one example, the oral appliance 100 may have dimensions in the region of 20 mm×10 mm×5 mm. The present invention is not limited to any particular dimension of oral appliance 100.

Referring to FIG. 4, in one example, the external processing unit 200 that receives the data from the oral appliance 100 is adapted to process the received data to determine whether the user U (FIGS. 1-3) has bruxism-like conditions. The external processing unit 200 may compare the received signal data against one or more predetermined sets of bruxism determination criteria. In this way, the oral appliance 100 is able to provide data to an external processing unit 200 so as to indicate to the user U or a dental professional whether the user U has bruxism-like conditions. The oral appliance 100 therefore enables the user U or dental professional to determine whether the user U suffers from bruxism. The user U or dental professional can then determine an appropriate strategy for treating or managing the bruxism of the user U. In one example, the oral device 100 is able to process the sensing data to determine whether the user U has bruxism-like conditions. The result of this determination can then be transmitted or otherwise provided to an external processing unit 200.

The oral appliance 100 of the present invention is not just for use in indicating whether the user U suffers has bruxism-like conditions. The oral appliance 100 is able to be used in several other applications as outlined below. The existing oral appliances do not appear to be able to provide these additional functionalities, or at least are not able to as easily/effectively provide them.

In one example, the oral appliance 100 is able to generate a stimulus in response to sensing the at least one part of the facial muscle complex being brought towards the sensing arrangement 101. The stimulus may act to help discourage the user U from chewing, clenching or grinding their teeth. The stimulus may be used to help the user U manage their bruxism.

Figure 6:
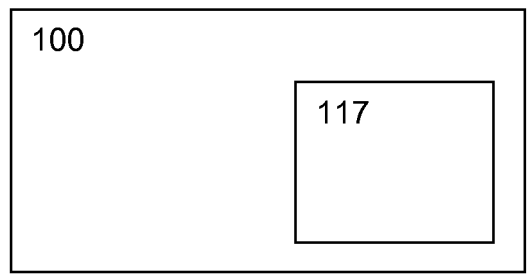
FIG. 6 is a simplified schematic diagram of an oral appliance in accordance with an example embodiment.

Referring to FIG. 6, in one example the oral appliance 100 may activate an actuator 117 to apply a stimulus to the user U (FIGS. 1-3) in response to the at least one part of the facial muscle complex being brought towards the sensing arrangement 101. The actuator 117 may generate a physical stimulus. The stimulus may be a vibrational stimulus. The actuator 117 may be part of the oral appliance 100 or may be part of a separate external processing unit 200. In another example, the oral appliance 100 may apply an electrical stimulus to the user U in response to the at least one part of the facial muscle complex being brought towards the sensing arrangement 101. The electrical stimulus may help unconsciously or subconsciously discourage the user U from chewing, clenching, or grinding their teeth. In this example the actuator 117 of the oral appliance 100 comprises an electrode arrangement 117 for applying the electrical stimulus to the user U. In another example, the electrode arrangement is part of a separate external processing unit 200. In another example, the oral appliance 100 may activate an alarm in response to detecting the at least one part of the facial muscle complex being brought towards the sensing arrangement 101. The alarm may be an audible alarm. In this example, the actuator 117 of the oral appliance 100 comprises an alarm generation unit 117 for generating the alarm. In another example, the alarm generation unit may be part of a separate external processing unit 200.

In one example, the oral appliance 100 is able to be used as an assistive technology device to help assist users with limited muscle functionality control the operation of an external processing unit 200. Users with limited muscle control, such as those suffering from neuromotor disorders, often having limited muscular function, and therefore the oral appliance 100 may enable more efficient use of the voluntary muscular activity available to them. In particular, the oral appliance 100 is able to function/serve as a clench activated clicker for controlling the external processing unit 200. The oral appliance 100 is able to detect the user U clenching their jaw by sensing the at least one part of the facial muscle complex being brought towards the sensing arrangement 101. In response, the oral appliance 100 is able to transmit a control signal to the external processing unit

200. The external processing unit 200 may be a computing device running dedicated assistive software programmes or may be a dedicated assistive device. The external processing unit 200 is then controlled based on the transmitted control signal.

Figure 7:
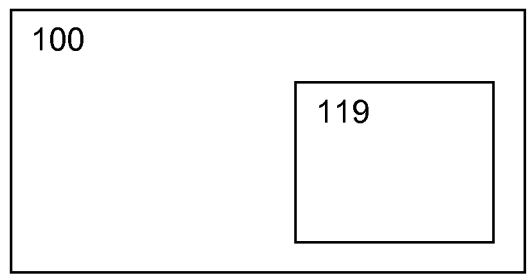
FIG. 7 is a simplified schematic diagram of an oral appliance in accordance with an example embodiment.

Referring to FIG. 7, in one example the oral appliance 100 comprises an actuator in the form of an applicator 119 for applying a medicament to the user U (FIGS. 1-3). The applicator 119 may be adapted to apply the medicament to the tissue surface of the user U, such as the buccal tissue. In some examples, the applicator 119 comprises one or more needles for injecting the medicament beneath the tissue surface of the user U. The one or more needles may be microneedles. The controller 111 is adapted to control the applicator 119 in response to the sensing arrangement 101 sensing the at least one part of the facial muscle complex being brought towards the sensing arrangement 101. In this way, the controller 111 controls the applicator 119 to apply medicament when the sensing arrangement 101 senses movement of the facial muscle complex associated with the user U clenching their jaw, grinding their teeth or chewing.

Significantly, the oral appliance 100 is able to be used as a drug delivery device, which is trigged to deliver the medicament (the drug) in response to the at least one part of the facial muscle complex being brought towards the sensing arrangement 101. The drug delivery may be initiated voluntarily by the user U in response to the user U bringing their at least one part of the facial muscle complex towards the sensing arrangement 101 such as by clenching their jaw. In addition, the drug delivery may be initiated when the user U involuntarily moves their at least one part of the facial muscle complex towards the sensing arrangement 101. This involuntary movement may be due to the user U suffering from a seizure which results in the jaw of the user U clenching.

In one example, the oral appliance 100 is positioned intra-orally in a position such that the oral appliance 100 contacts the buccal tissue when the at least one part of the facial muscle complex is brought towards the sensing arrangement 101. The oral appliance 100 in this example is positioned on the buccal aspect of the posterior teeth. This enables the oral appliance 100 to act as a transbuccal drug delivery device. In one example, the oral appliance 100 comprises microneedles to advantageously facilitate optimal transbuccal drug delivery.

In one example, the oral appliance 100 is able to be used to indicate whether the user U is suffering from epilepsy-like conditions. Users suffering from epilepsy may experience nocturnal seizures which involve clenching of the jaw during sleep. The oral appliance 100 is able to detect this clenching of the jaw by detecting the at least one part of the facial muscle complex being brought towards the sensing arrangement 101. The oral appliance 100 is therefore able to help indicate whether the user U is suffering from epilepsy like conditions during their sleep.

In one example, the oral appliance 100 may be used to assist in the treatment of epilepsy. The oral appliance 100 may be adapted to perform an action involving applying a medicament to the user U in response to the oral appliance 100 or an external processing unit 200 which receives the sensing data from the oral appliance 100 determining that the user U is suffering from epilepsy-like conditions. In one example, the oral appliance 100 comprises the applicator 119 for applying the medicament. In another example, the medicament may be applied by an external processing unit 200 separate to the oral appliance 100. The external processing unit 200 may be adapted to apply the medicament in response to receiving a command from the oral appliance 100.

Figure 8:
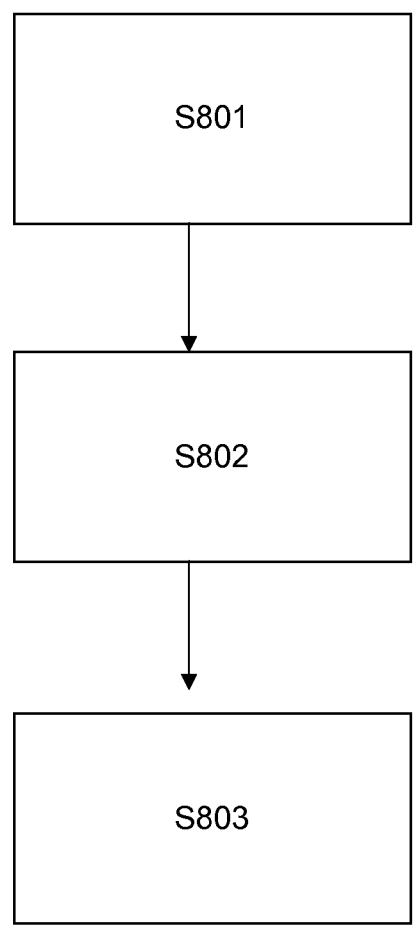
FIG. 8 is a simplified diagram of a method of controlling an oral appliance in accordance with an example embodiment.

Referring to FIG. 8, there is shown a method of controlling the oral appliance 100 according to one example.

In Step 801, the oral appliance 100 is at least temporarily orally fixated in the mouth of the user U.

In Step 802, the oral appliance 100 senses, with the sensing arrangement 101, the at least one part of the facial muscle complex being brought towards the sensing arrangement 101.

In Step 803, the oral appliance 100 is controlled to perform an action in response to sensing the at least one part of the facial muscle complex being brought towards the sensing arrangement 101.

As used above, the at least one part of the facial muscle complex being brought towards the sensing arrangement 101 includes the situation where the at least one part of the facial muscle complex, or an object associated with the at least one part of the facial muscle complex (such as the buccal tissue) is already in contact with the sensing arrangement 101 even when the at least one part of the facial muscle is in a relaxed, non-contracted state. In this situation, it will be appreciated that as the at least one part of the facial muscle complex contracts, it will be brought further towards the sensing arrangement 101 such that it applies additional force on the sensing arrangement 101 which can be detected by the sensing arrangement 101.

Although the above generally refers to use of the oral appliance 100 in a user having teeth, it will be appreciated that the oral appliance will still function where the user does not have one or more teeth or indeed has one or more dentures instead of teeth.

Although a few preferred embodiments of the present invention have been shown and described, it will be appreciated by those skilled in the art that various changes and modifications might be made without departing from the scope of the invention, as defined in the appended claims.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of controlling an oral appliance, the oral appliance comprising a sensing arrangement disposed in proximity to at least one part of a facial muscle complex of a user, the method comprising:
sensing, with the sensing arrangement, the at least one part of the facial muscle complex being brought towards and physically interacting with the sensing arrangement, wherein the sensing the physical interaction of the at least one part of the facial muscle complex with the sensing arrangement comprises sensing the at least one part of the facial muscle complex contacting the sensing arrangement as a result of deformation of the at least one part of the facial muscle complex; and
in response to the sensing, controlling the oral appliance to perform an action.

2. A method as claimed in claim 1, wherein sensing the at least one part of the facial muscle complex being brought towards the sensing arrangement comprises sensing one or more of whether the at least one part of the facial muscle complex has deformed, the number of deformations of the at least one part of the facial muscle complex over a period of time, the duration of one or more deformations of the at least one part of the facial muscle complex, and the degree of one or more deformations of the at least one part of the facial muscle complex.

3. A method as claimed in claim 2, wherein sensing the degree of the deformations of the at least one part of the facial muscle complex comprises sensing the pressure exerted on the sensing arrangement as a result of the at least one part of the facial muscle complex being brought towards the sensing arrangement.

4. A method as claimed in claim 1, wherein controlling the oral appliance to perform an action comprises controlling the oral appliance to generate a signal for transmission or storage.

5. A method as claimed in claim 4, wherein the signal indicates one or more of whether the at least one part of the facial muscle complex has deformed, the number of deformations of the at least one part of the facial muscle complex over a period of time, the duration of one or more deformations of the at least one part of the facial muscle complex, and the degree of one or more deformations of the at least one part of the facial muscle complex.

6. A method as claimed in claim 4, wherein controlling the oral appliance to perform an action comprises controlling the oral appliance to transmit the signal to an external processing unit.

7. A method as claimed in claim 1, wherein controlling the oral appliance to perform an action comprises controlling an actuator of the oral appliance.

8. A method as claimed in claim 1, wherein the at least one part of the facial muscle complex comprises at least one part of the masseter muscle complex.

9. An oral appliance comprising:
a sensing arrangement adapted to be disposed in proximity to at least one part of a facial muscle complex of a user; and
a controller adapted to control the oral appliance to perform an action in response to the sensing arrangement sensing the at least one part of the facial muscle complex being brought towards and physically interacting with the sensing arrangement, wherein the sensing the physical interaction of the at least one part of the facial muscle complex with the sensing arrangement comprises sensing the at least one part of the facial muscle complex contacting the sensing arrangement as a result of deformation of the at least one part of the facial muscle complex.

10. An oral appliance as claimed in claim 9, wherein the oral appliance is adapted to be at least temporarily orally fixated in the mouth of the user.

11. An oral appliance as claimed in claim 9, further comprising:
a transmitter,
wherein the controller is adapted to control the transmitter to transmit a signal to an external processing unit in response to the sensing arrangement sensing the at least one part of a facial muscle complex being brought towards and physically interacting with the sensing arrangement.

12. An oral appliance as claimed in claim 9, further comprising:
an actuator;
wherein the controller is adapted to control the actuator in response to the sensing arrangement sensing the at least one part of the facial muscle complex being brought towards and physically interacting with the sensing arrangement.

13. A system comprising:
an oral appliance as claimed in claim 9; and
an external processing unit arranged to interact with the oral appliance in response to the oral appliance performing the action.

* * * * *